United States Patent
Fujita (10) Patent No.: US 6,614,918 B1
(45) Date of Patent: Sep. 2, 2003

(54) APPARATUS FOR INSPECTING LIGHT-AND-SHADE PORTIONS AND METHOD THEREOF

(75) Inventor: Minoru Fujita, Kawasaki (JP)

(73) Assignee: Toshiba Engineering Corporation, Kawasaki (JP)

( * ) Notice: Subject to any disclaimer, the term of this patent is extended or adjusted under 35 U.S.C. 154(b) by 0 days.

(21) Appl. No.: 09/285,746

(22) Filed: Apr. 5, 1999

(30) Foreign Application Priority Data

Jul. 21, 1998 (JP) .......................................... 10-205251

(51) Int. Cl.$^7$ ................................................ G06K 9/00
(52) U.S. Cl. ...................... 382/112; 382/141; 382/111; 356/237.1; 250/559.01
(58) Field of Search ................................ 382/100, 112, 382/111, 141, 149; 250/559, 571, 559.01–559.49; 356/237.1–237.6, 429, 430; 700/143

(56) References Cited

U.S. PATENT DOCUMENTS

| | | | |
|---|---|---|---|
| 3,843,890 A | * 10/1974 | Anthony et al. | 250/559.49 |
| 4,685,139 A | * 8/1987 | Masuda et al. | 382/112 |
| 5,068,799 A | * 11/1991 | Jarrett, Jr. | 364/507 |
| 5,091,963 A | * 2/1992 | Litt et al. | 382/8 |
| 5,138,671 A | * 8/1992 | Yokoyama | 382/172 |
| 5,377,279 A | * 12/1994 | Hanafusa et al. | 382/141 |
| 5,774,177 A | * 6/1998 | Lane | 348/88 |
| 6,091,847 A | * 7/2000 | Chiu et al. | 382/149 |
| 6,236,057 B1 | * 5/2001 | Shishido | 250/559 |
| 6,535,621 B1 | * 3/2003 | Fujita | 382/112 |

FOREIGN PATENT DOCUMENTS

| | | |
|---|---|---|
| EP | 0 311 991 A2 | 4/1989 |
| EP | 0 428 751 A1 | 5/1991 |
| EP | 0 731 599 A2 | 9/1996 |

* cited by examiner

Primary Examiner—Bhavesh M. Mehta
Assistant Examiner—Aaron Carter
(74) Attorney, Agent, or Firm—McGinn & Gibb, PLLC (57) ABSTRACT

A light-and-shade inspection apparatus and method therefor include an image pick-up device for picking up an image of an object across a dimension (e.g., width) thereof to produce an image data, a projection operational portion for calculating a projection data by adding together a predetermined number of the image data, the image data being produced at each scan of the image pick-up device at a predetermined position along the width of the object, a background lightness operational portion for calculating, based on the projection data produced by the projection operational portion, a background lightness of the object across its width, and a difference operational portion for subtracting the background lightness produced by the background lightness operational portion from the image data produced by the image pick-up device, thereby substantially eliminating variations of the background lightness across the width of the object from the image data.

23 Claims, 7 Drawing Sheets

PROJECTION DATA

SMOOTHED DATA

LIGHTNESS VARIATION
IN TRANSVERSE DIRECTION

APPARATUS FOR INSPECTING LIGHT-AND-SHADE PORTIONS AND METHOD THEREOF

BACKGROUND OF THE INVENTION

1. Field of the Invention

The present invention relates to a light-and-shade inspection apparatus and method for use in inspection of light-and-shade defects on a plain material roll (or web) based on an image data which is produced by an image pick-up device picking up an image of the web (e.g., paper, film, nonwoven fabric, etc.) having a certain width and traveling in one direction. More particularly, the invention relates to a light-and-shade inspection apparatus for inspecting light-and-shade portions and a method for implementing it, by which variations of a background brightness (e.g., luminance) occurring in a width (e.g., transverse) direction of the web can be accurately eliminated.

2. Description of the Related Art

Figures 8, 9, 10:
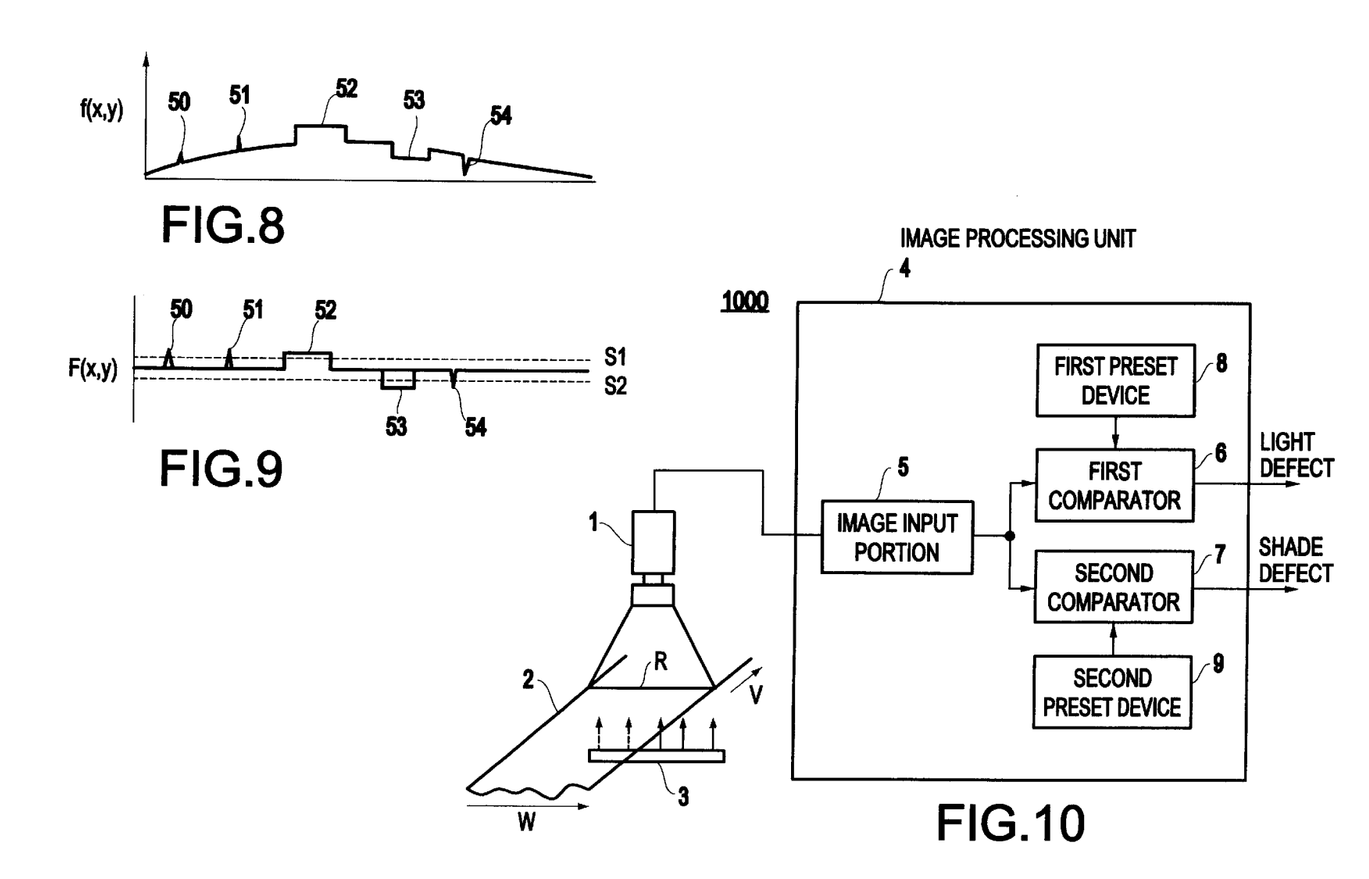
FIG. 8 is a schematic diagram showing a picked-up image data.
FIG. 9 is a schematic diagram showing an operation of a comparator portion 40 of the light-and-shade inspection apparatus 100 of FIG. 1.
FIG. 10 is a block diagram showing a conventional light-and-shade inspection apparatus 1000.

FIG. 10 is a block diagram showing a conventional light-and-shade inspection apparatus 1000 used for inspecting a web 2. Apparatus 1000 includes a line-sensor camera 1 for picking up an image of the web 2 as an inspected object having a constant width and traveling in one direction, an illuminator 3 for illuminating a zone picked up by the camera 1, and an image processing device 4 for processing data of an image picked up by the camera 1 and inspecting light and shade defects on the web.

The line-sensor camera 1 includes, for example, a photodetector array of 1024 elements (e.g., a charge-coupled device (CCD)) disposed along a line. Specifically, the camera 1 is disposed upwardly of a central portion of the web so that the photodetectors are arranged in a line array across the web in a transverse (width) direction thereof and in parallel with the transverse direction. The illuminator 3 is disposed downwardly of the web 2 (e.g., on the underside of the web), so as to illuminate the zone to be picked up by the camera 1 from a rear surface of the web 2.

The image processing device 4 includes an image input portion 5 for performing an analog-to-digital (A/D)-conversion of a picked-up image signal outputted from the camera 1 and for capturing into the image processing device 4 the resultant (digitized) signal as an image data of luminance (e.g., lightness or brightness) information (e.g., specified with 256 levels of gray), a first comparator 6 coupled to an output of the image input portion 5 and adapted for comparing the image data with a first threshold value S1, and a second comparator 7 also coupled to the output of the image input portion 5 and adapted for comparing the image data with a second threshold value S2. The first threshold value S1 is preset in a first preset device 8 and the second threshold value S2 is preset in a second preset device 9.

Figure 11:
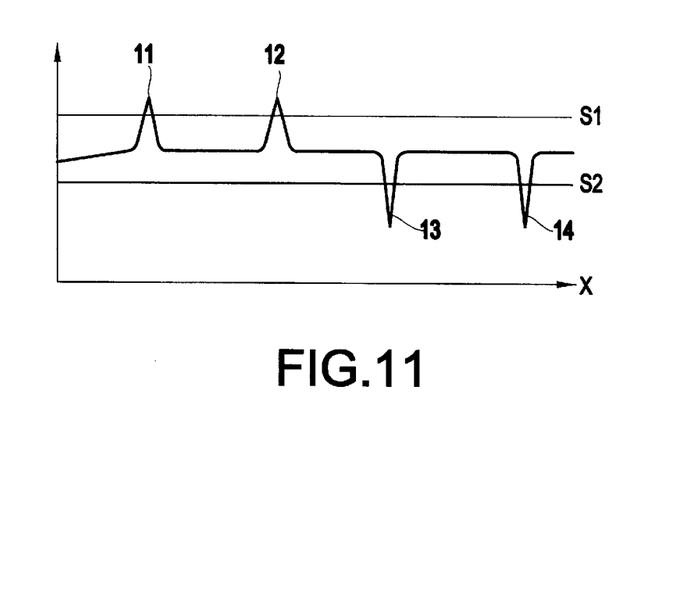
FIG. 11 is a schematic diagram showing an operation of the conventional light-and-shade inspection apparatus 1000.

Referring to FIG. 11, an operation of the above-mentioned light-and-shade defect inspection apparatus 1000 will be described. In FIG. 11, a time-chart shows a lightness pattern of the image data obtained with one scan of the line-sensor camera 1. In the time chart of FIG. 11, the horizontal axis (x) indicates a position on the web 2 in the transverse direction, whereas the vertical axis indicates a degree of lightness of the image data.

If the web 2 has thereon a defect which tends to increase a lightness (e.g., a hole or a flaw), there appears in the image data a high lightness portion (e.g., reference numeral 11 or 12), as shown in FIG. 11. The comparator 6 detects a light defect when this portion is higher than the first threshold value S1. On the other hand, if the web 2 has thereon a defect which tends to lower its lightness (e.g., caused by a stain, adhered foreign matter, etc.), there appears in the image data a low lightness portion (or a shade portion) indicated by numeral 13 or 14, as shown in FIG. 11. The comparator 7 detects a shade defect when this portion is lower than the second threshold value S2.

Thus, the conventional light-and-shade defect inspection apparatus 1000 inspects the presence or absence of light-and-shade defects by comparing the image data with two threshold values.

Figure 12:
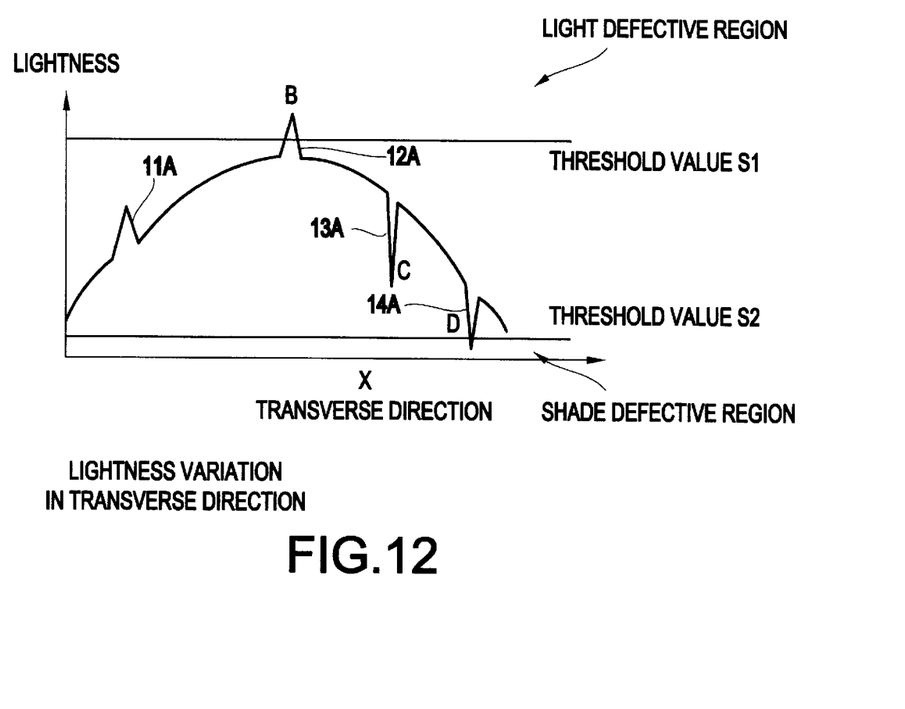
FIG. 12 is a schematic diagram showing a problematic operation of the conventional light-and-shade inspection apparatus 1000.

However, when the line-sensor camera 1 picks up an image of the web 2 while the web 2 is illuminated by the illuminator 3 as shown in FIG. 10, the lightness of the web 2 tends to increase at central and neighboring portions thereof due to characteristics of camera lenses and a condensing degree of the illuminator. As a result, the obtained image data of the picked-up image may vary, as shown in FIG. 12 rather than that of FIG. 11. In that case, if threshold values for the image data of FIG. 12 are fixed as S1, S2 shown in FIG. 11, defects such as numerals 11A, 13A of FIG. 12 may not be detected, despite being detected correctly as true defects, since they are apparently smaller in magnitude or size than their corresponding threshold values.

Figure 13:
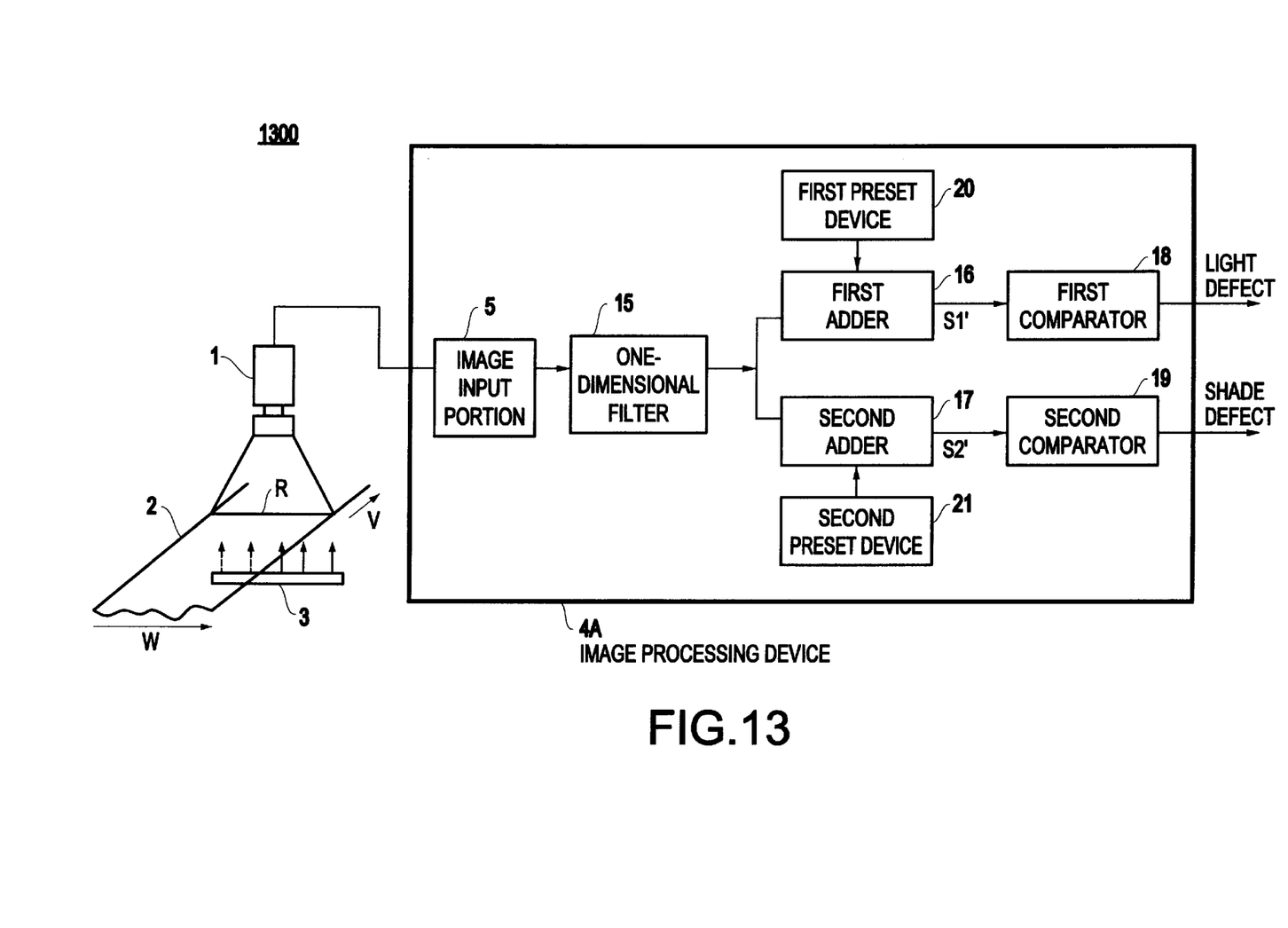
FIG. 13 is a functional block diagram showing another conventional light-and-shade inspection apparatus 1300.

In view of the foregoing, a light-and-shade defect inspection apparatus 1300 as shown in FIG. 13 is known to eliminate the above-mentioned problem.

Referring to FIG. 13 wherein like reference numerals of FIG. 10 refer to similar parts, an image processing device 4A is shown.

Image processing device 4A includes an image input portion 5 for performing an A/D-conversion of a picked-up image signal outputted from the camera 1 and for capturing the resultant (digitized) signal as an image data into the image processing device 4A, a one-dimensional filter 15, coupled to an output of the image input portion 5, for performing a smoothing processing of 1024 image data obtained by one scan of the camera 1, a first adder 16, coupled to an output of the filter 15, for obtaining a first threshold value S1' by adding a first preset value to a smoothed signal outputted from the filter 15, and a second adder 17, similarly coupled to the filter 15, for obtaining a second threshold value S2' by adding a second preset value to the smoothed signal.

Furthermore, the image processing device 4A includes a first comparator 18, coupled to outputs of the image input portion 5 and the first adder 16, for comparing the image data with the first threshold value S1', and a second comparator 19, coupled to outputs of the image input portion 5 and the second adder 17, for comparing the image data with the second threshold value S2'. Here, the first threshold value S1 is preset in a first preset device 20 and the second threshold value S2 is preset in a second preset device 21.

With this configuration, the first and second preset values in the first and second preset devices 20 and 21 are respectively added to the smoothed signal obtained by the one-dimensional filter 15, thereby allowing the respective preset values S1' and S2' to be changed in response to the web's lightness (luminance) variation across the width thereof. Hence, the defect 11A and 13A, which is not detected as defects in FIG. 12, can be detected as shown in FIG. 14.

Figure 14:
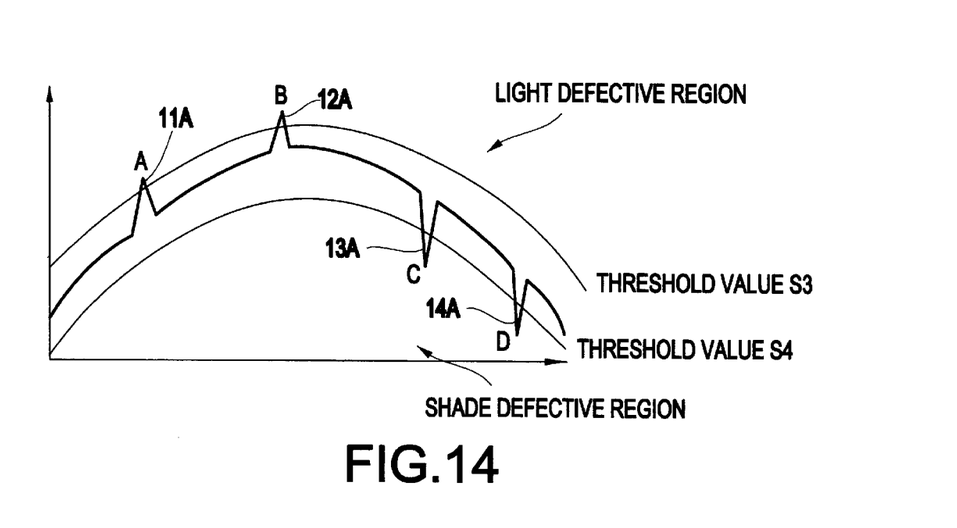
FIG. 14 is schematic diagram showing an operation of the conventional light-and-shade inspection apparatus 1300 of FIG. 13.

However, despite the improved apparatus, a problem associated with the known improved light-and-shade defect inspection apparatus 1300 resides in that an area of each defect shown in FIG. 11 or 14 increases. It is noted that a length L of the defect appearing as an image data may be equal to or longer than an average length of data outputted from the one-dimensional filter 15. In that case, a lightness variation due to the defect may be processed similarly to a lightness variation of the background lightness, and the threshold value will vary as the defect lightness. As a result, the calculation of the background lightness is affected by the defect lightness, thereby causing an error in a calculated value.

Figure 15:
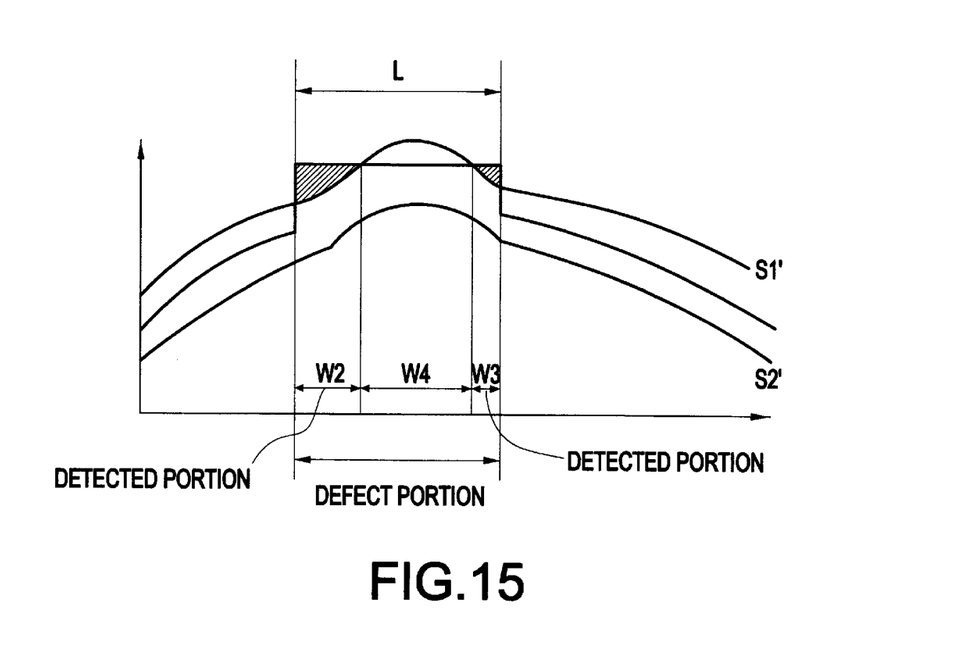
FIG. 15 is a schematic diagram showing a problematic operation of the conventional light-and-shade inspection apparatus 1300 of FIG. 13.

For example, a problem occur that only portions W2, W3 could be detected as being defective within a zone W1 which zone should be essentially detected as a defect but a central portion W4 might not be detected as being defective.

The above problem is caused because an image pick-up range across the width of the web covered by the line-sensor camera is restricted, and the area of the defect increases with respect to the average length of data used in the image picked-up range. Also, this problem becomes worse as the defective area becomes larger.

Accordingly, the conventional light-and-shade defect inspection apparatus 130 possesses a significant deficiency that a light-and-shade defect inspection of a web having thereon various size defects (e.g., ranging from a small defective area to a large defective area), cannot be performed by using only one optical system.

SUMMARY OF THE INVENTION

In view of the foregoing and other problems of the conventional systems and methods, the present invention is directed to a light-and-shade inspection apparatus and method with a high reliability and low cost. With the present invention, defects on a web can be inspected reliably by using only one optical system and by accurately eliminating the background lightness regardless of a size of the defects (e.g., ranging from a small area to a large area). As a result, a light-and-shade inspection is provided at a low manufacturing cost and with a high accuracy.

To overcome the above-mentioned problems, in a first aspect of the present invention, a light-and-shade inspection apparatus is provided for picking up an image of an object to be inspected having a constant width and traveling in one direction to produce an image data and then performing a light-and-shade inspection of the object based on the image data, and which includes:

an image pick-up device for picking up an image of an object across a overall width thereof to produce an image data;

a projection operational portion for calculating a projection data by adding together the image data by a predetermined number, the image data being produced at each scan of the image pick-up device at a predetermined position along the width of the object;

a background lightness operational portion for calculating a background lightness of the object across its width based on the projection data produced by the projection operational portion; and a difference operational portion for subtracting the background lightness produced by the background lightness operational portion from the image data produced by the image pick-up device, thereby eliminating variations of the background lightness across the width of the object from the image data.

With this arrangement, an amount of additional data can be freely increased for the calculation of the projection data in response to the number of scans. As a result, the number of data used in calculating the background lightness can be increased substantially in comparison with the number of data for the defective area. Thus, the present invention reduces the adverse affects of defects from the calculation of the background lightness, thereby removing variations of the background lightness from the image data with high accuracy.

Additionally, in the light-and-shade inspection apparatus according to the present invention, the background lightness operational portion includes:

a filter for smoothing the projection data across the width of the object produced by the projection operational portion; and a normalization portion for dividing the smoothed data by the predetermined number of the added image data, thereby calculating the background lightness.

Further, the light-and-shade inspection apparatus according to the present invention further includes a comparator portion adapted for comparing an output from the difference operational portion with a predetermined value to detect light-and-shade defects.

Hence, a highly reliable light-and-shade inspection apparatus is provided capable of detecting a defect having a certain lightness regardless of the defect's size and with high accuracy.

Furthermore, in the light-and-shade inspection apparatus according to the present invention, the image pick-up device includes a line-sensor camera directed to the object and arranged across the width of the object. Even if such a line-sensor camera is employed, the amount of data for the background lightness calculation can be increased in response to the number of scans of the camera, thereby allowing the background lightness to be calculated with a high accuracy. Also, the use of this line-sensor camera allows the manufacturing cost to be reduced in comparison with the use of an area-sensor camera.

Furthermore, in the light-and-shade inspection apparatus according to the present invention, the predetermined number of the image data to be added together at the projection operational portion can be changed in response to a light-and-shade defective area size.

With this arrangement, for a large defective area, the number of the image data to be added together is correspondingly increased and, for a small defective area, that number is correspondingly decreased, thereby allowing the background lightness to be obtained with only one optical system with high accuracy and efficiency and without any affect of the defective area size. Also, this arrangement is inexpensive. Incidentally, changing the predetermined number is performed by operating and varying a preset number N in the projection operational portion.

Furthermore, in the light-and-shade inspection apparatus according to the present invention, the background lightness operational calculation at the background lightness operational portion is performed at the completion of a predetermined number of scans by the image pick-up device, and the difference operational calculation at the difference operational portion is performed with respect to an inputted image data by using the background lightness calculated through the background operational calculation which has been performed immediately prior to that input of the image data.

With this arrangement, an accurate background lightness may be produced by following variations of the background lightness occurring during movements of the object or over time, and further accuracy, reliability and stability of the background lightness can be ensured.

In another aspect of the invention, a light-and-shade inspection method according to the present invention, wherein an object to be inspected having a constant width and traveling in one direction is picked up to produce an image data thereof and then inspecting based on the image data light-and-shade portions on the object, includes:

picking up an image of an object across a width thereof to produce an image data;

calculating a projection data by adding together the image data by a predetermined number, each image data being produced at a predetermined position along the width of the object;

calculating a background lightness of the object across the width by performing smoothing and normalizing processing operations of the projection data; and eliminating variations of the background lightness across the width of the object from the image data by subtracting the calculated background lightness from the image data.

By implementing this method, an additional amount of data can be increased freely for calculating the projection data in response to the number of scans. As a result, the number of data for calculation of the background lightness can be increased substantially in comparison with the number of data for the defective area. Thus, adverse affects of defects are reduced from the calculation of the background lightness, thereby removing variations of the background lightness from the image data with high accuracy.

The present disclosure relates to subject matter contained in Japanese Patent Application No. 10-205251, filed Jul. 21, 1998, which is expressly incorporated herein by reference in its entirety.

BRIEF DESCRIPTION OF THE DRAWINGS

The above and other objects, features and advantages of the present invention will become apparent from the following detailed description of the invention taken in conjunction with the accompanying drawings in which.

DETAILED DESCRIPTION OF A PREFERRED EMBODIMENT OF THE PRESENT INVENTION

Hereinafter, a preferred embodiment of the present invention will be described in detail with reference to the accompanying drawings.

Figure 1:
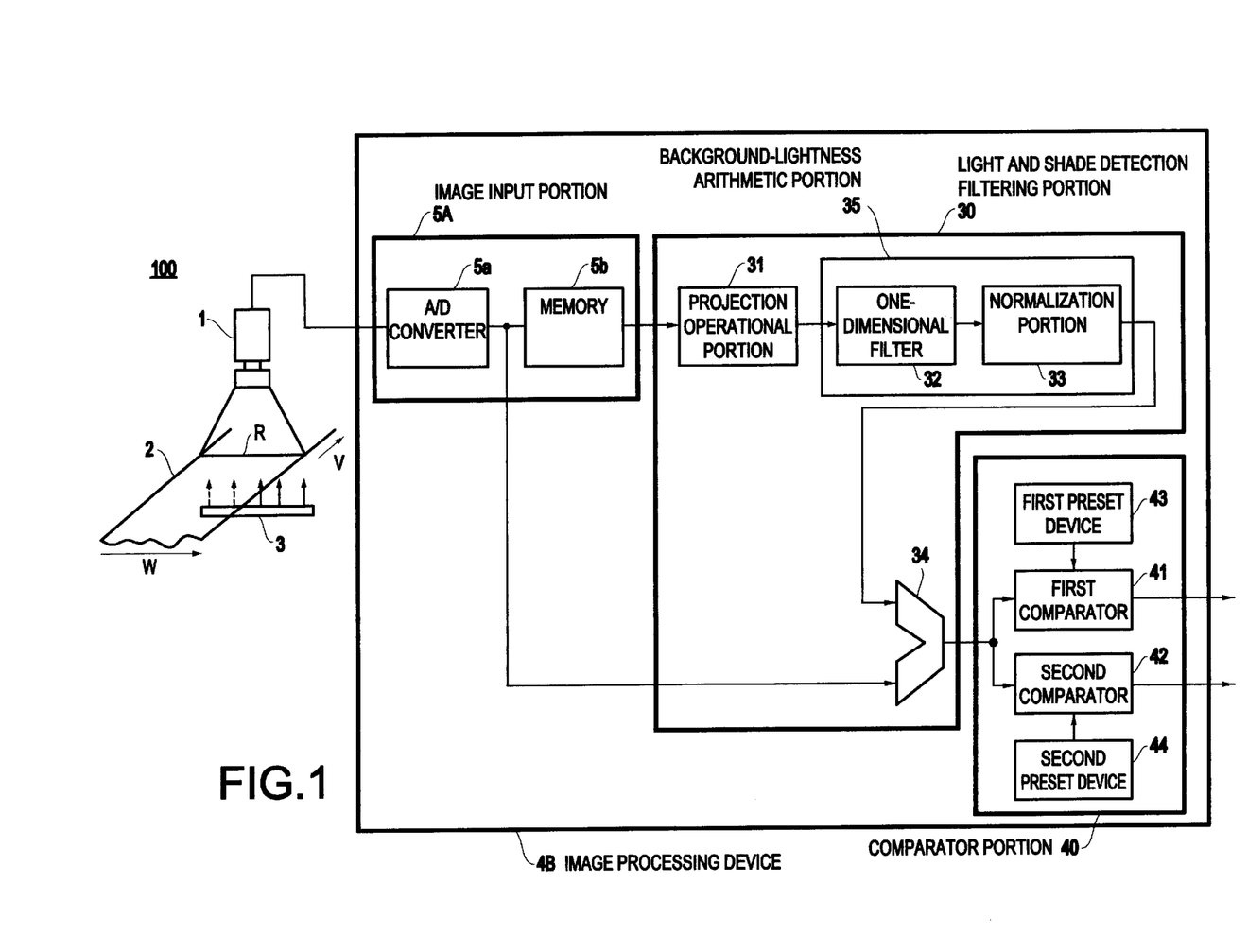
FIG. 1 is a block diagram showing a preferred embodiment of a light-and-shade inspection apparatus 100 according to the present invention.

Referring to FIG. 1; a light-and-shade inspection apparatus 100 of the present invention applied to a light-and-shade defect inspection apparatus for a web inspection is illustrated in the form of a functional block diagram.

The light-and-shade defect inspection apparatus 100 includes a line-sensor camera 1 for picking up an image of a web 2 as an object to be inspected having a substantially constant width and traveling in one direction, an illuminator 3 for illuminating a zone on the web over which the camera 1 picks up the web image, and an image processing device 4B by which an image data, based on the web image picked up by the camera 1, is processed to inspect light-and-shade defects on the web.

The line-sensor camera 1 includes 1024 photoreceptors (e.g., a charge-coupled device (CCD)) arranged in an array along a line and disposed above a central portion in a width direction or across the width of the web 2 and in a parallel relation to the width direction. The illuminator 3 is placed below the web 2 so as to illuminate (e.g., light up) the web zone to be picked up by the camera 1 from a back side of the web 2.

As shown in FIG. 1, the image processing device 4B includes an image input portion 5A coupled to an output of the camera 1, a light-and-shade detection filtering portion 30 coupled to an output of the image input portion 5A, and a comparator portion 40 coupled to an output of the light-and-shade detection filtering portion 30.

The image input portion 5A includes an analog-to-digital (A/D) converter 5a for performing an A/D conversion of an analog signal of the picked-up image outputted from the camera 1 and for producing a digitized image signal, and a memory 5b for storing, as image data, image signals produced by digitizing the analog image signals obtained through a plurality of scans of the camera 1. As a result, the image signals picked up by the camera 1 are captured in the image processing device 4B.

The light-and-shade detection filtering portion 30 includes a projection operational portion 31 coupled to an output of the image input portion 5A, a one-dimensional filter 32 coupled to an output of the projection operational portion 31, a normalization portion 33 coupled to an output of the filter 32, and a subtracter 34 coupled to outputs of the normalization portion 33 and the A/D converter 5a. The one-dimensional filter 32 and the normalization portion 33 form a background-lightness operational (e.g., arithmetic) portion 35.

The comparator portion 40 includes a first preset device 43 in which a first threshold value S1 is preset, a second preset device 44 in which a second threshold value S2 is preset, a first comparator 41, coupled to outputs of the subtracter 34 and the first preset device 43, for comparing the output of the subtracter 34 with the first threshold value S1, and a second comparator 42, coupled to outputs of the subtracter 34 and the second threshold value S2, for comparing the output of the subtracter 34 with the second threshold value S2.

Hereinbelow, the preferred embodiment will be described with reference to FIGS. 2 to 8.

Figure 2:
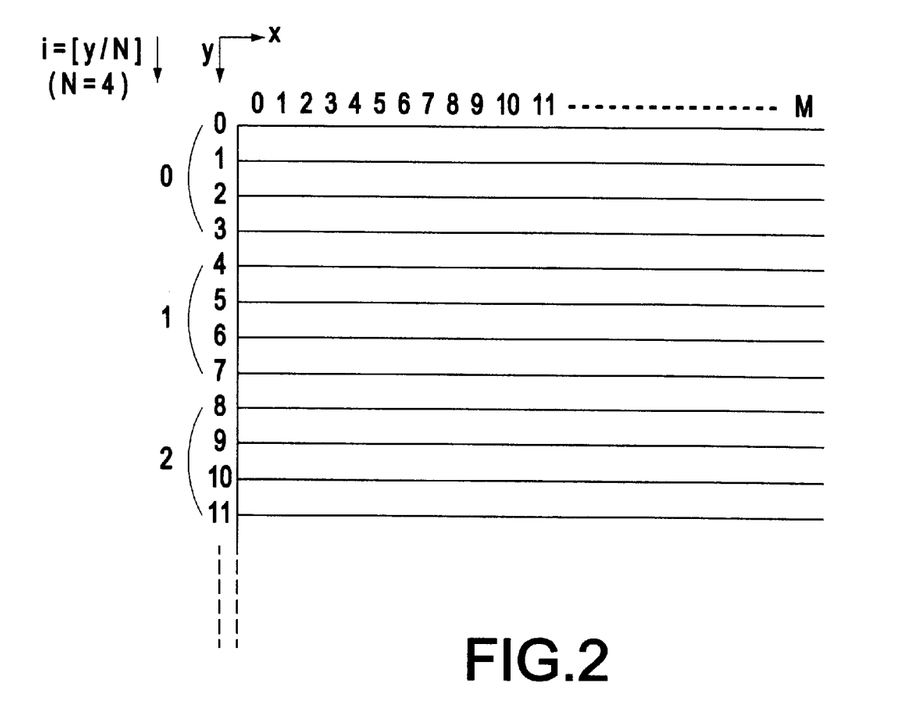
FIG. 2 is a schematic diagram showing a data structure which is captured into a memory of the light-sand-shade apparatus 100 of Figure.

FIG. 2 shows an exemplary data structure which is captured into the memory 5b. In FIG. 2, a horizontal axis (e.g., X-axis) illustrates a region of data positions which is scanned through one scan of the line-sensor camera 1. An X-coordinate indicates a position of the line-sensor which corresponds to a positional coordinate on the web 2 in the width direction. In the example of FIG. 2, a positional coordinate of x=0 corresponds to an end or its neighboring portion of the web, whereas a positional coordinate of x=M corresponds to the other end or its neighboring portion of the web. In this embodiment, it is assumed that 1024 photoreceptors are used to pick up an image across the web's width (e.g., M=1024).

In FIG. 2, a vertical axis (e.g., Y-axis) indicates the number of scans of the camera 1, and has reference numerals 1 through 11 as the scan number affixed thereon. For example, the scan number 0 indicates a first scan of the camera. In FIG. 2, i numbers are labeled, each being organized every N scans sequentially. The i number can be expressed by i=[y/N] with the Gaussian notation [ ].

In this embodiment, the number of N is set at 4 but this number N may be selectively adjusted if desired. For example, if a defective area is large, the number N may be increased according to its defective area size.

As a data structure as shown in FIG. 2, the scan numbers from 0 to 11 are shown, but the number of data stored into the memory is the scan number 0-N(4) with which the calculation (e.g., the projection operation) is performed.

Figure 3:
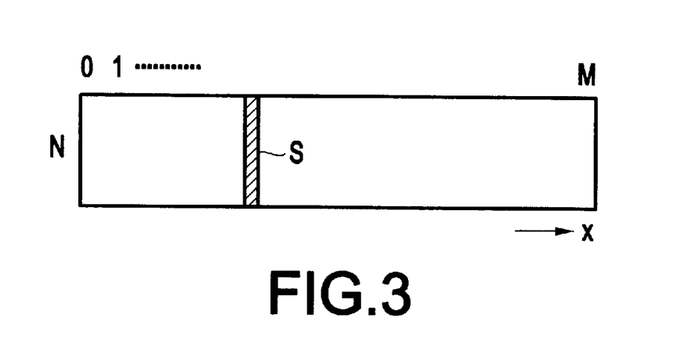
FIG. 3 is a schematic diagram showing an operation of a projection operational portion of the light-and-shade inspection apparatus 100 of FIG. 1.
Figure 4:
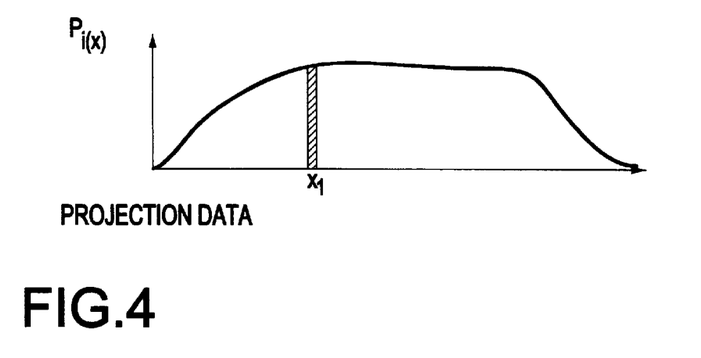
FIG. 4 is a schematic diagram showing projection data.

The projection operational portion 31 as shown in FIG. 1 will determine a projection by using scan data of N lines (N×M) at a time from the memory as being representative of its operation in FIG. 3. As shown in FIG. 3, N image data at each X-coordinate are added together to create a hatching portion S (i.e., image data at a predetermined position in the transverse direction of the object to be inspected are added together until the number of its image data reaches a predetermined number), thereby providing a projection data as shown in FIG. 4.

This operation or calculation is expressed by the following equation (1):

$$Pi = \Sigma f(x, y) \quad (1)$$

where i=[y/N], N defines a number of lines to be added together with this addition being performed up to the N line numbers counting from y=N·i, (i.e., up to N·i+N−1).

Figure 5:
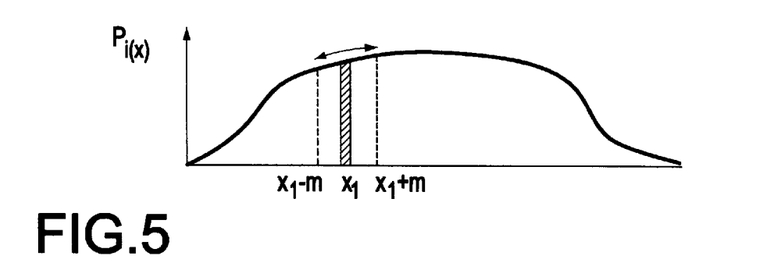
FIG. 5 is a schematic diagram showing an operation of a one-dimensional filter 32 of the light-and-shade apparatus 100 of FIG. 1.
Figure 6:
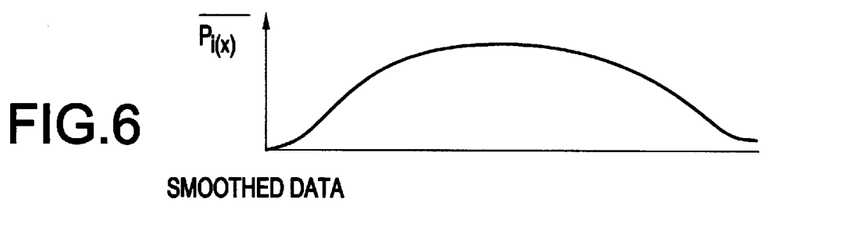
FIG. 6 is a schematic diagram showing smoothed data as an output from the one-dimensional filter 32 of the light-and-shade inspection apparatus 100 of FIG. 1.

Next, the one-dimensional filter 32 performs the smoothing of the projection data, produced from the projection operational portion 31, in a range between +m and −m from its X-coordinate ($x_1$) in the X-axis direction, thereby producing a smoothed data as shown in FIG. 6. This operation or calculation is defined by the following equation (2):

$$\overline{Pi}(x) = (\Sigma pi(x-m+j)g(j)/(\Sigma g(j)) \quad (2)$$

where the operational addition is performed with j=0~2 m, and g is representative of a filter function but it may be replaced by a constant.

Figure 7:
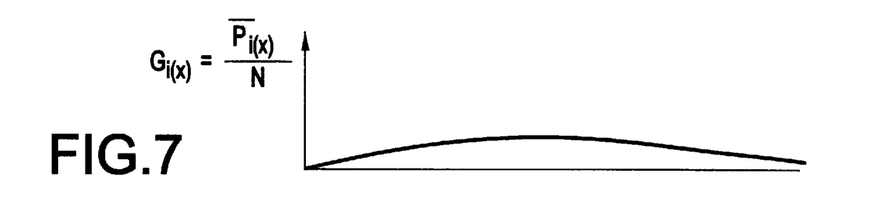
FIG. 7 is a schematic diagram showing a background lightness (luminance) as an output from a normalization portion 33 of the light-and-shade inspection apparatus 100 of FIG. 1.

The normalization portion 33 divides the smoothed data by the number N of lines to be added together, thereby obtaining a background lightness Gi(x), as shown in FIG. 7. This operation is given by the following equation (3):

$$Gi(x) = \overline{Pi}(x)/N \quad (3)$$

The subtracter 34 subtracts the obtained background lightness Gi(x) from image data f(x, y) newly inputted from the camera 1 to the image input portion 5A. This operation or calculation is defined by the following equation (4):

$$F(x,y) = f(x,y) - Gi(x), \; I = [y/N] \quad (4)$$

With this operation, the inputted image data f(x,y) as shown in FIG. 8 is changed into or expressed by a function F(x,y) from which variations of the background lightness are eliminated. As clear from FIGS. 8 and 9, light defects 50, 51 and a shade defect 54 are each shown as relatively small defective areas, and a light defect 52 and a shade defect 53 are each shown as relatively large defective areas. Specifically, from FIG. 9 clarified by cancellation of the background lightness, it will be appreciated that the defective area's influence on the background lightness is negligible.

Subsequently, the first comparator 41 compares this function F(x,y) with the first threshold value S1 and then the image data (area) is judged to be a light defect if the function F(x,y) is higher than the first threshold value 1. Also, the second comparator 42 compares the function F(x,y) with the second threshold value S2 and then the image data (area) is judged to be a shade defect if the function F(x,y) is lower (e.g., larger in its absolute value) than the second threshold value S2.

Incidentally, the above-mentioned operation by the light-and-shade detection filtering portion 30 is performed every predetermined number N of scans of the camera 1. Further, a difference operation by the subtracter 34 is performed with respect to the inputted image data f(x,y) using the background lightness (e.g., i=[y/N] in equation (4)) obtained by the background lightness operation performed immediately prior to that input of the image data f(x,y). However, the background lightness operation after completion of a first-time predetermined number N of scans may be performed each time one scan is completed without causing any problem.

Due to this configuration, an accurate background lightness may be produced despite variations in the background lightness occurring during movements of the object to be inspected or over time. Further, accuracy, reliability and stability of the background lightness are ensured with the present invention. According to the above scheme, the background lightness for a period will not be obtained until a first-time predetermined number N of scans is completed. However, empirical values could be used as the background lightness for that time period. Otherwise, it will be appreciated that the lightness detection may be negligible for that period.

As mentioned above, the difference operation is performed with respect to next image data inputted subsequent to the image data with which the calculation of the background lightness has been previously performed. Thus, the difference operation is performed between the current inputted image data and the immediately previous inputted image data. Further, the image data per se may be used, by which the background lightness is calculated, as one to be subtracted with that background lightness. Furthermore, the memory 5b is provided for temporarily storing the image data to be used for the projection operation. However, it is possible to add together data at the respective x-coordinates in response to each scan and to perform the projection operation in real time. Furthermore, the present invention can be sufficiently realized by an area-sensor camera in place of the line-sensor camera.

According to the method of the present invention, first an object to be inspected is picked up across its transverse direction to obtain its image data, then the number of image data which can be obtained every scan at a predetermined position are added together up to a predetermined number to calculate a projection data, then the projection data is processed by smoothing and normalizing processing operations to calculate a background lightness across the transverse direction of the object, and finally the background lightness is subtracted from the image data to eliminate variations of the background lightness across the transverse direction of the object from the image data.

Thus, the number of data may be increased freely for the calculation of the projection data in response to the number of scans. As a result, the number of data for calculating the background lightness can be substantially increased in comparison with the number of data for producing the defective area, Accordingly, adverse affects of defects are reduced from the calculation of the background lightness, thereby providing a highly reliable light-and-shade inspection apparatus and method of removing variations of the background lightness from the image data and detecting light-and-shade defects regardless of their sizes and with high accuracy.

While the principles of the invention have been described above in connection with a specific embodiment, and particular modifications thereof, it is to be clearly understood that this description is made only by way of example and not as a limitation on the scope of invention. Thus, while the invention has been described in terms of a preferred embodiment, those skilled in the art will recognize that the invention can be practiced with modification within the spirit and scope of the appended claims.

What is claimed is:

1. A light-and-shade inspection apparatus for picking up an image of an object to be inspected having a substantially constant width and traveling in a first direction to produce an image data and then performing a light-and-shade inspection of the object based on the image data, comprising:
   a line-sensor camera for picking up an image of an object across an overall width thereof to produce an image data;
   a projection operational portion for calculating a projection data by adding together the image data by a predetermined number of lines in said traveling direction, said image data being produced at each scan of said line-sensor camera at a predetermined position along the width of the object;
   a background lightness operational portion for calculating a background lightness of the object across its width, based on the projection data produced by said projection operational portion; and
   a difference operational portion for subtracting the background lightness produced by said background lightness operational portion from the image data produced by said line-sensor camera, thereby substantially eliminating variations of the background lightness across the width of the object from the image data.

2. The light-and-shade inspection apparatus as claimed in claim 1, wherein said background lightness operational portion includes:
   a filter for smoothing the projection data across the width of the object produced by said projection operational portion; and
   a normalization portion for dividing the smoothed data by the predetermined number of lines in said traveling direction of the added image data, thereby calculating the background lightness.

3. The light-and-shade inspection apparatus as claimed in claim 1, further comprising a comparator portion for comparing an output from said difference operational portion with a predetermined value to detect light-and-shade defects.

4. The light-and-shade inspection apparatus as claimed in claim 2, further comprising a comparator portion for comparing an output from said difference operational portion with a predetermined value to detect light-and-shade defects.

5. The light-and-shade inspection apparatus as claimed in claim 1, wherein said line-sensor camera is directed to the object and arranged across the width of the object.

6. The light-and-shade inspection apparatus as claimed in claim 2, wherein said line-sensor camera is directed to the object and arranged across the width of the object.

7. The light-and-shade inspection apparatus as claimed in claim 3, wherein said line-sensor camera is directed to the object and arranged across the width of the object.

8. The light-and-shade inspection apparatus as claimed in claim 4, wherein said line-sensor camera is directed to the object and arranged across the width of the object.

9. The light-and-shade inspection apparatus as claimed in claim 1, wherein the predetermined number of lines in said traveling direction of the image data to be added together at said projection operational portion is selectively adjustable in response to a defective area size.

10. The light-and-shade inspection apparatus as claimed in claim 2, wherein the predetermined number of lines in said traveling direction of the image data to be added together at said projection operational portion is selectively adjustable in response to a defective area size.

11. The light-and-shade inspection apparatus as claimed in claim 3, wherein the predetermined number of lines in said traveling direction of the image data to be added together at said projection operational portion is selectively adjustable in response to a defective area size.

12. The light-and-shade inspection apparatus as claimed in claim 4, wherein the predetermined number of lines in said traveling direction of the image data to be added together at said projection operational portion is selectively adjustable in response to a defective area size.

13. The light-and-shade inspection apparatus as claimed in claim 5, wherein the predetermined number of lines in said traveling direction of the image data to be added together at said projection operational portion is selectively adjustable in response to a defective area size.

14. The light-and-shade inspection apparatus as claimed in claim 6, wherein the predetermined number of lines in said traveling direction of the image data to be added together at said projection operational portion is selectively adjustable in response to a defective area size.

15. The light-and-shade inspection apparatus as claimed in claim 7, wherein the predetermined number of lines in said traveling direction of the image data to be added together at said projection operational portion is selectively adjustable in response to a defective area size.

16. The light-and-shade inspection apparatus as claimed in claim 1, wherein the background lightness operational calculation by said background lightness operational portion is performed at every completion of a predetermined number of scans by said image pick-up device, and
   wherein the difference operational calculation by said difference operational portion is performed with respect to an inputted image data by using the background lightness calculated through said background operational calculation which has been performed immediately prior to input of the image data.

17. The light-and-shade inspection apparatus as claimed in claim 1, wherein the background lightness operational calculation by said background lightness operational portion is performed at every completion of a predetermined number of lines in said traveling direction of scans by said line-sensor camera.

18. The light-and-shade inspection apparatus as claimed in claim 1, wherein the difference operational calculation by said difference operational portion is performed with respect to an inputted image data by using the background lightness calculated through said background operational calculation which has been performed immediately prior to input of the image data.

19. A light-and-shade inspection apparatus, comprising:

a line-sensor camera for scanning a dimension of an object, and for producing image data at each scan of said line-sensor camera;

a projection data calculator for calculating a projection data by adding together a predetermined number of lines in a traveling direction of the image data;

a background luminance calculator for calculating a background luminance of the object across said dimension, based on the projection data produced by said projection data calculator; and a subtractor for subtracting the background luminance produced by said background luminance calculator from the image data produced by said line-sensor camera, wherein said dimension comprises a width of said object.

20. An image processing device for a light-and-shade inspection apparatus, comprising:

a projection data calculator for calculating a projection data by adding together a predetermined number of lines in a traveling direction of image data input thereto, said image data produced by scanning a dimension of an object, and respective ones of said image data being produced at each scan of said object;

a background luminance calculator for calculating a background luminance of the object across said dimension thereof, based on the projection data produced by said projection data calculator; and a difference calculator for subtracting the background luminance produced by said background luminance calculator from the image data input to said projection data calculator, wherein said dimension comprises a width of said object.

21. An image processing device for a light-and-shade inspection apparatus, comprising:

means for calculating a projection data by adding together a predetermined number of lines in a traveling direction of image data input thereto, said image data produced by scanning a dimension of an object, and respective ones of said image data being produced at each scan of said object;

means for calculating a background luminance of the object across said dimension thereof, based on the projection data produced by said projection data calculating means; and means for subtracting the background luminance produced by said background luminance calculating means from the image data input to said projection data calculating means, wherein said dimension comprises a width of said object.

22. A method of light-and-shade inspection of an object, comprising:

picking up an image of an object across a dimension thereof;

calculating a projection data by adding together a predetermined number of lines in a traveling direction of the image data, each image data being produced at a predetermined position along the dimension of the object;

calculating a background lightness of the object across the dimension thereof by smoothing and normalizing the projection data; and subtracting the calculated background lightness from the image data, thereby substantially eliminating variations of the background lightness across the dimension of the object from the image data, wherein said dimension comprises a width of said object.

23. The light-and-shade inspection apparatus as claimed in claim 1, wherein said overall width is a distance between a first edge and a second edge of said object.

* * * * *